United States Patent [19]

DiGiulio

[11] 4,157,876
[45] Jun. 12, 1979

[54] LOCKABLE ARTICULATED JOINT

[76] Inventor: Mario DiGiulio, c/o Spectra Industries Corp., 405 Baily Rd., Yeadon, Pa. 19050

[21] Appl. No.: 886,897

[22] Filed: Mar. 15, 1978

Related U.S. Application Data

[62] Division of Ser. No. 741,798, Nov. 15, 1976, Pat. No. 4,088,129.

[51] Int. Cl.² .................. F16C 11/06; F16D 1/12
[52] U.S. Cl. ........................ 403/90; 403/123; 403/125
[58] Field of Search .......... 403/56, 76, 77, 87, 403/90, 123, 124, 125; 128/80 R, 80 A, 80 E, 88; 3/21, 31; 285/263

[56] References Cited

U.S. PATENT DOCUMENTS

| | | | |
|---|---|---|---|
| 898,391 | 9/1908 | Peterson | 403/90 X |
| 1,136,397 | 4/1915 | Bloch | 128/80 A UX |
| 1,446,164 | 2/1923 | D'Eyraud | 403/90 X |
| 1,788,083 | 1/1931 | Church | 403/124 X |
| 2,369,849 | 2/1945 | Phillips | 285/263 |
| 2,436,678 | 2/1948 | Somers | 403/123 |
| 2,465,751 | 3/1949 | Robins | 403/123 X |
| 2,585,342 | 2/1952 | Morgan | 128/80 A |
| 3,149,863 | 9/1964 | Melton et al. | 403/125 |
| 3,306,640 | 2/1967 | Melton et al. | 403/77 |
| 3,422,462 | 1/1969 | Finneston | 3/21 |
| 4,088,348 | 5/1978 | Shemtov | 285/263 X |

Primary Examiner—Wayne L. Shedd
Attorney, Agent, or Firm—George A. Smith, Jr.

[57] ABSTRACT

This orthopedic appliance for correcting a wide variety of lower extremity deformities comprises: a bar which is scored so that it can be broken to provide a bar of a desired length; lockable articulated joints at both ends of the bar; releasable clips for rapidly attaching and detaching the articulated joints to and from the bottom of the patient's shoes; index markings allowing the articulated joints to be accurately adjusted and locked in the desired position; nesting extension attachments; and stabilizer rods for maintaining plantar or dorsi flexion and insuring that the device is not defeated by bending the knees.

Included in the appliance is a lockable articulated joint utilizing a hollow spherical member clamped between a spherical socket and a spherical locking member. The radius of curvature of the locking member is slightly greater than that of the inside of the hollow spherical member, and the radius of curvature of the outside of the hollow spherical member is likewise slightly greater than that of the socket.

3 Claims, 18 Drawing Figures

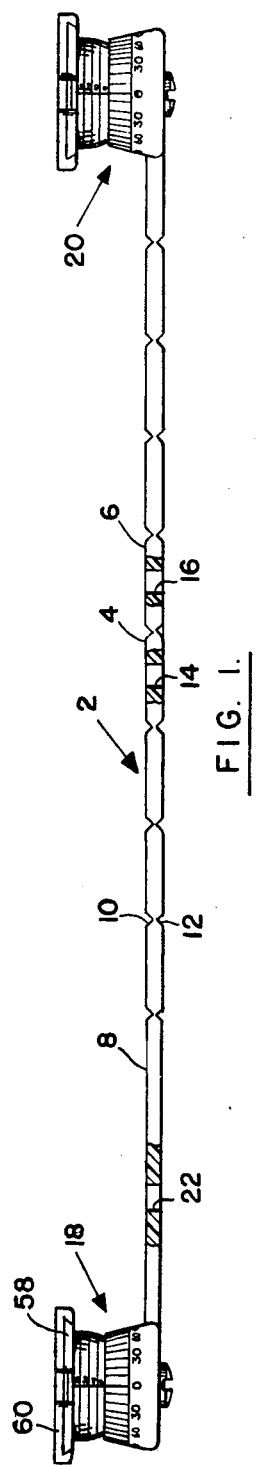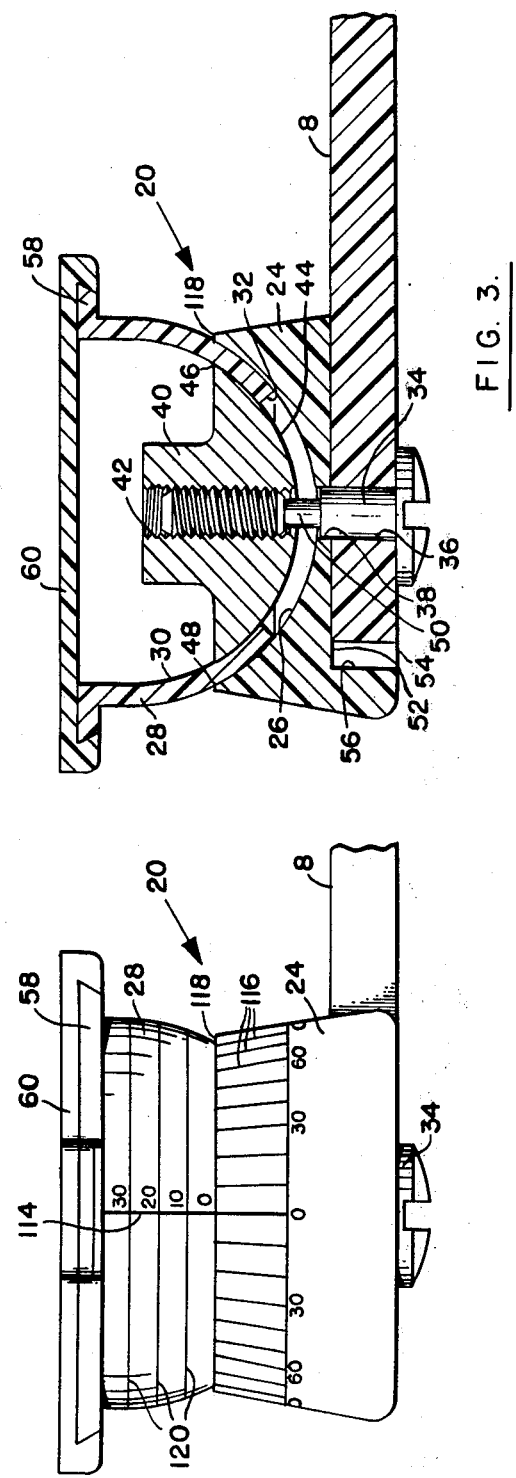

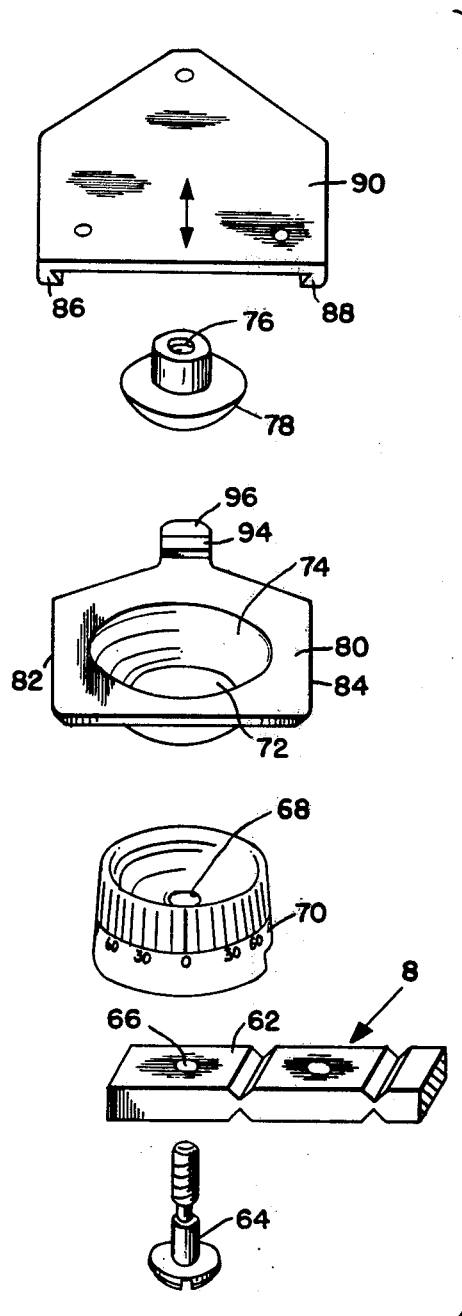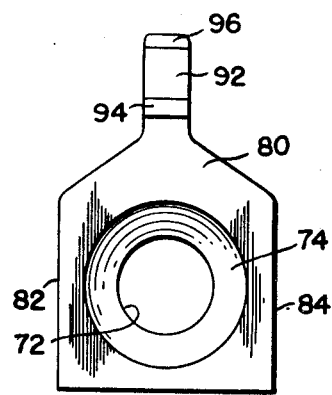
FIG. 5.
FIG. 4.
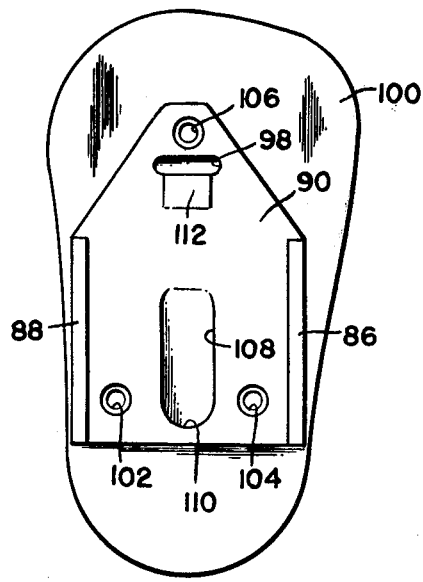
FIG. 6.

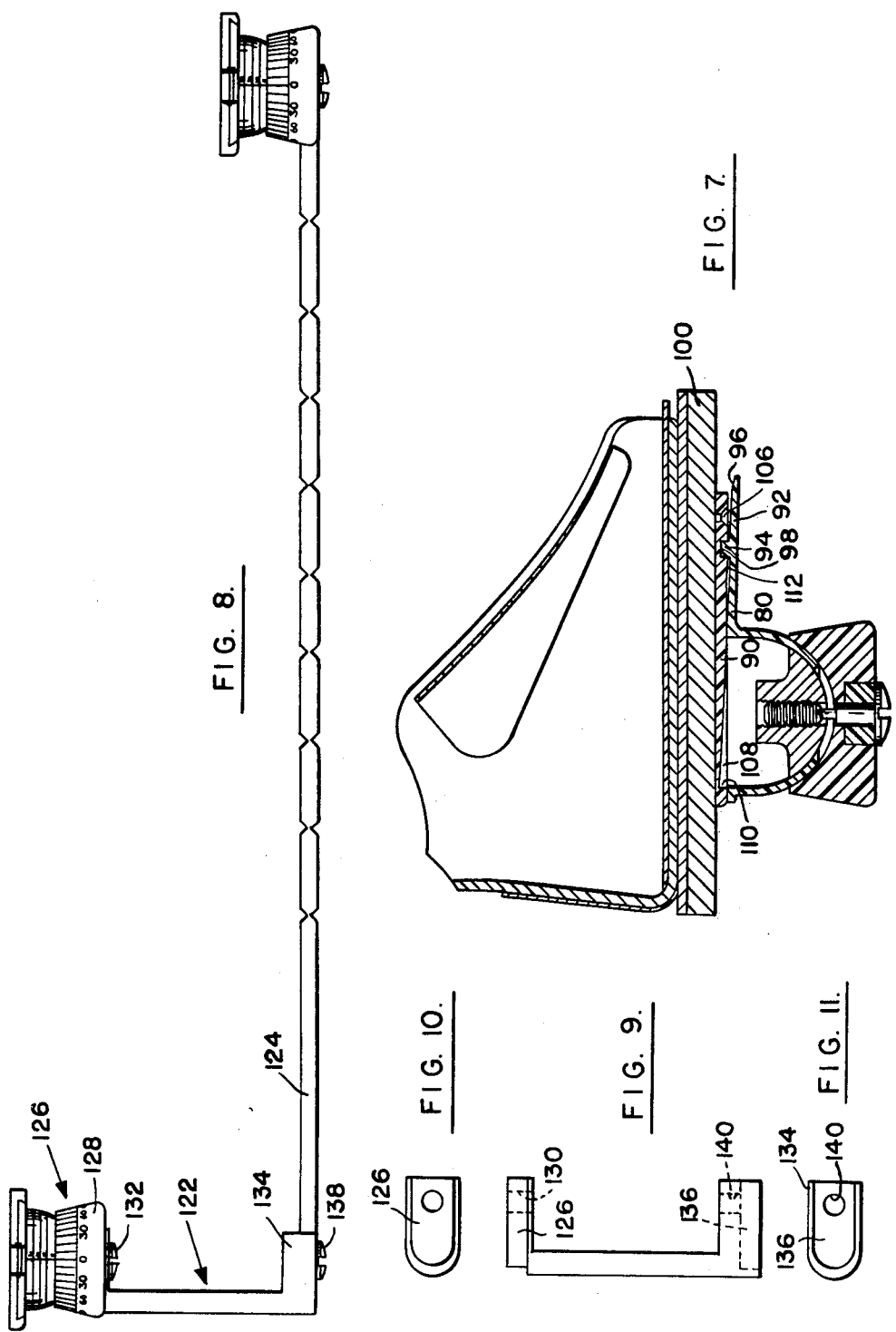

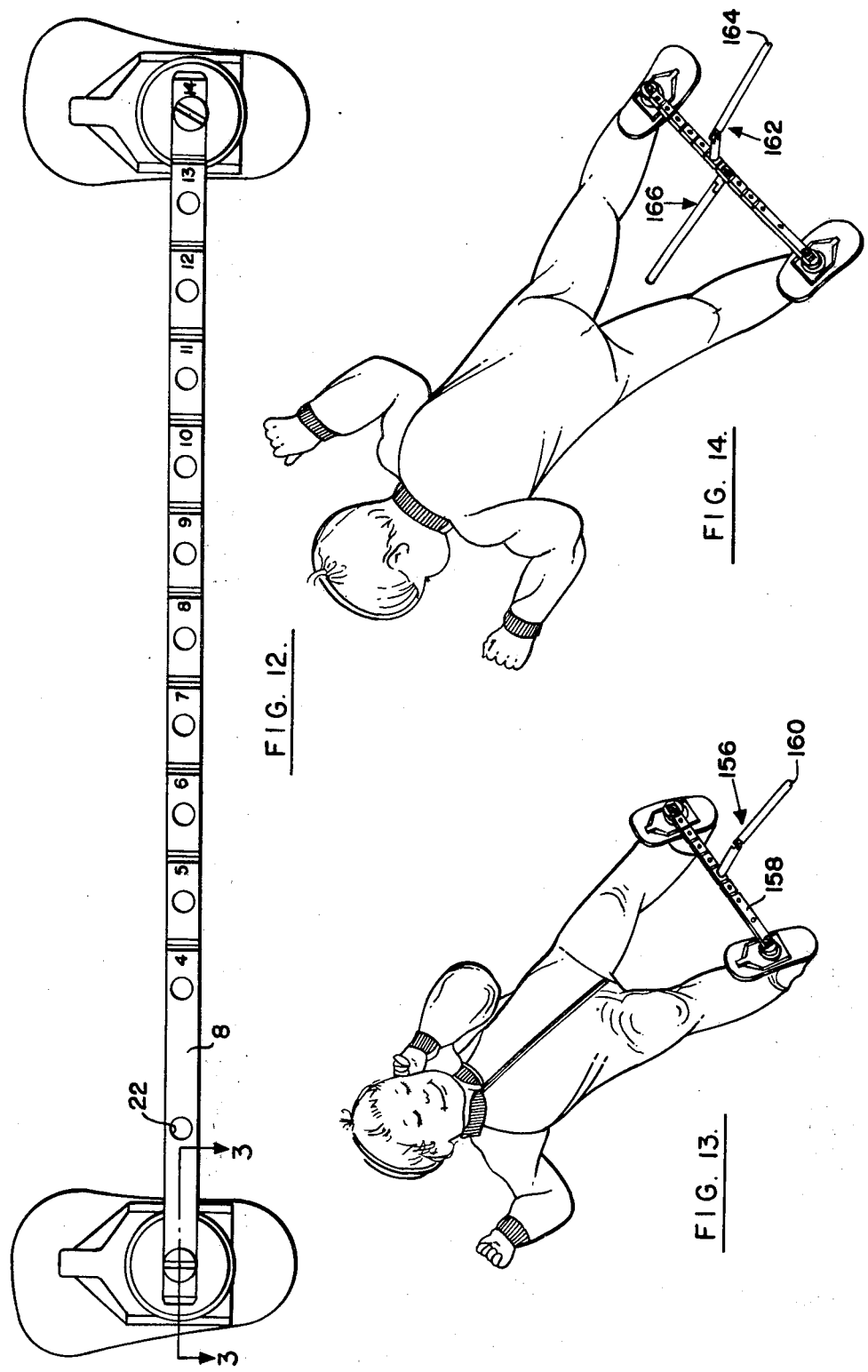

LOCKABLE ARTICULATED JOINT

CROSS-REFERENCE TO RELATED APPLICATIONS

This is a division of my copending application Ser. No. 741,798, filed Nov. 15, 1976, now U.S. Pat. No. 4,088,129, dated May 9, 1978.

SUMMARY OF THE INVENTION

This invention relates to corrective orthopedic appliances and particularly to improvements in the class of devices generally known as "Denis Browne Splints" or "night splints". The invention has utility in the correction of deformities of the lower extremities, especially in the newborn and the very young. The class of devices to which the invention relates is also designated "abduction braces", this term denoting devices adapted to be connected between the patient's feet and which hold the feet at a fixed distance from each other while performing a corrective function.

The invention also relates to a lockable articulated joint having utility not only in the particular foot orthosis appliance to be specifically described, but also having utility in various other applications such as in work holders, machine tools and the like. The articulated joint will be specifically described in the context of a foot orthosis appliance in order to illustrate one important application of the joint.

A typical Denis Browne splint comprises a rigid bar adapted to be connected between the feet of a patient, and means at either end of the bar for attachment to the patient's feet and maintaining the feet in the desired relationship to each other. In many instances, the rigid bar is of a fixed length, and therefore a large number of bars of different lengths must be kept on hand. For example, one commercially available device is available with any desired bar from four inches to ten inches in one inch increments and from ten inches to thirty-six inches in two inch increments. A number of adjustable bars have been proposed, but they are subject to considerable stress in use, and can be worked out of adjustment unless they are very carefully made and securely locked in the desired position.

The rigid bar is attached to the patient's shoes by various means. In some instances, plates are permanently riveted to the soles of the shoes, and attached to the bar by screws. The system of plates and bars requires the maintaining of the desired adjustment while the screws which attach the plates to the bar are being tightened. This makes accurate adjustment somewhat difficult. Consequently, once the adjustment is made, it is usually maintained, and the removal and replacement of the splint requires the removal and replacement of the patient's feet from the shoes while the shoes are attached to the splint.

Another system for attachment of the bar to the patient's feet requires the use of clamps which clamp the sides of the sole of the shoe. The clamps can be detached from the shoes without disturbing the adjustment of the splint, but it is difficult to reattach the splint to the shoes in the exact relationship desired.

Some conditions require the provision of means for spacing the bar from the bottoms of the feet by different fixed distances. So far as is known, no satisfactory means of doing so has yet been devised.

Certain conditions of the lower extremities require the maintenance of either of plantar (toe down) or dorsi (toe up) flexion on one or both feet. The ordinary Denis Browne splints are not capable of correcting such conditions, and while other devices exist for these conditions, using them in addition to the Denis Browne splint is difficult. Consequently it is difficult to correct some of the more complex deformities.

In accordance with the invention, the foot orthosis appliance preferably comprises an elongated rigid bar transversely scored at a plurality of spaced locations along its length so that the bar can be manually broken by the application of a bending moment to provide a shortened bar having one of a number of predetermined discrete lengths. It includes means adapted to be secured to the bar at both ends thereof, and at both ends of a part thereof, if a part is used, for attachment to the feet of a patient. By providing a scored bar, the need for keeping a large number of bars of different lengths on hand is eliminated.

Another important feature of the invention lies in the use of a pair of lockable articulated joint means, each having a first part adapted to be secured to the bar, a second part articulably secured to the first part, and means locking the first and second parts in any desired relationship within a range. Clip means are fixed to the said second part of each of the articulated joints for releasable rigid attachment to a corresponding shoe clip. Shoe clips are also provided, each being adapted to be secured to the sole of a shoe, preferably by means of an adhesive. Each of the shoe clips is adapted for releasable rigid attachment to a corresponding one of the clip means on the articulated joints. The articulated joints can be kept locked in the prescribed condition, or can be adjusted easily to a newly prescribed condition. As the shoes can be attached to and detached from the brace readily by means of the clip means and shoe clips, it is unnecessary to disturb the adjustment of the articulated joints each time the brace is removed or applied. Likewise, it is unnecessary to remove the shoes from the patient's feet each time the brace is applied and removed. The shoe clips and the clip means are locked to each other in exactly the same relationship each time they are engaged so that the prescribed settings are exactly reproduced.

Accurate reproduction of the prescribed setting is achieved with the aid of a preferred form of lockable articulated joint in conjunction with the detachable clip means and shoe clip. Each lockable articulated joint comprises a socket member, a hollow spherical member engaged therein, and a locking member arranged to clamp the hollow spherical member against the socket member. Each of the socket members has index means visibly located adjacent the edge of its inner surface, and each of the hollow spherical members is provided with visible index means on its spherical outer surface adapted to be viewed in conjunction with the index means on the corresponding socket member for reproducing predetermined relationships between the hollow spherical members and their corresponding socket members.

The lockable articulated joint can be locked at any desired angular relationship of its socket and hollow spherical member within the available range of articulation. It is made to lock much more securely than lockable joints heretofore available by adopting a particular dimensional relationship between its respective parts. Specifically the radius of curvature of the outer surface of the hollow spherical member is made slightly greater than that of the socket. Likewise the inner surface of the hollow member, which is also spherical, and which is engaged by a spherical locking member is provided with a radius of curvature which is slightly less than that of the locking member.

In cases where the bar must be spaced from the bottom of a foot by a fixed distance, an extension is used which consists of a rigid member secured in substantially perpendicular relationship to the bar and adapted to attach to the socket member of one of the articulated joints. This extension spaces the articulated joint from the bar by the required distance. The design of the articulated joint socket and the design of the bar are not affected, and therefore the same articulated joint, and the same bar can be used either with or without the extension.

To maintain plantar or dorsi flexion using the device in accordance with the invention, a stabilizer rod is provided which is adapted to be rigidly secured to the bar, approximately midway between the patient's feet, and in perpendicular relation to the bar. This rod always extends generally parallel to the patient's legs, and it is adapted to be attached to the bar in either direction, so that it extends either upwardly toward the patient's head or downwardly in the opposite direction. Its end contacts the surface of the patient's bed and limits the flexion of the feet. Preferably the stabilizer comprises two hinged parts which can be locked together in any desired relationship to determine the limit of flexion. A second stabilizer rod extending in the opposite direction may be necessary to prevent the patient from defeating the flexion-limiting stabilizer by bending his knees.

The principal objects of the invention are the provision of a foot orthosis appliance which presents a practical solution to one or more of the above-mentioned problems with prior art braces, and also to provide an appliance which is applicable to a wide variety of lower extremity conditions, which is of uniform design, and which is simple and relatively low in cost, thereby resulting in a decreased cost to the patient's family, and to the government where the latter is involved.

It is also an object of the invention to provide an improved lockable articulating joint in which the articulable elements can be locked together much more securely than the corresponding elements of prior lockable articulating joints.

Other objects of the invention will be apparent from the following detailed description when read in conjunction with the drawings.

BRIEF DESCRIPTION OF THE SEVERAL VIEWS OF THE DRAWING

FIG. 1 is an elevational view of an assembled appliance in accordance with the invention, including the bar, the lockable articulated joints, and the shoe clips adapted to be glued to the soles of the patient's shoes;

FIG. 2 is an enlarged elevational view showing the details of the left-hand end of FIG. 1;

FIG. 3 is a vertical section of the apparatus of FIG. 2, taken on a plane which cuts the bar longitudinally into two symmetrical parts (see FIG. 12 for the location of the plane);

FIG. 4 is an exploded rear view of the articulated joint and shoe clip assembly at the right-hand side of FIG. 1;

FIG. 5 is a top plan view of an element comprising the hollow spherical member of one of the articulated joints and a clip means for engagement with a shoe clip;

FIG. 6 is a bottom plan view of a shoe with a shoe clip secured thereto;

FIG. 7 is a vertical section taken on a plane perpendicular to the bar, and illustrating the manner in which a shoe clip is removably engaged with clip means on the hollow spherical member of an articulated joint;

FIG. 8 is an elevational view of a brace, having an extension at one end for spacing the universal joint from the bar;

FIG. 9 is an elevational view of the extension;

FIG. 10 is a top plan view of the extension;

FIG. 11 is a bottom plan view of the extension;

FIG. 12 is a bottom plan view of a brace in accordance with the invention, showing the brace attached to the soles of a pair of shoes;

FIG. 13 is an oblique perspective showing the brace in use, and particularly illustrating the stabilizer rod;

FIG. 14 is another oblique perspective showing an alternative arrangement of the stabilizer rod;

FIG. 17 is a vertical section of a modified lockable articulated joint adapted for use in supporting electrical lighting fixtures and the like.

DETAILED DESCRIPTION

Figure 16:
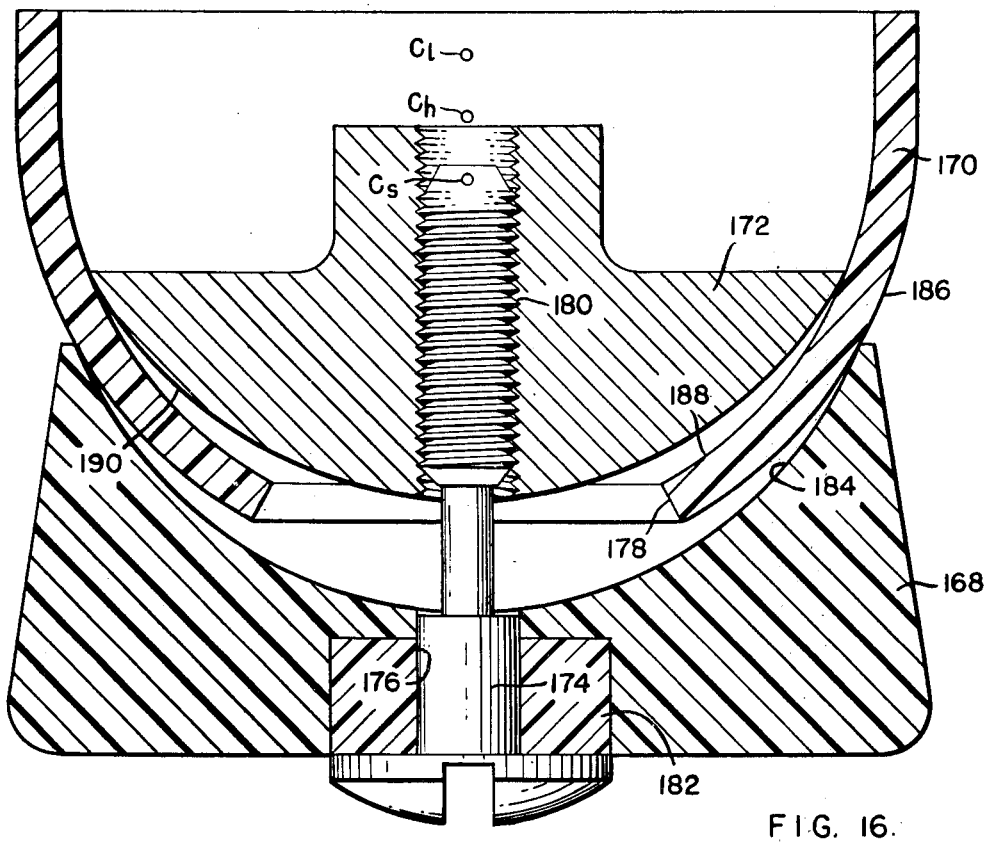
FIG. 16 is a vertical section of the lockable articulated joint, illustrating by exaggeration, the dimensional relationship of the various spherical surfaces.

FIG. 1 shows an elongated bar 2 having a generally rectangular cross-section, and divided into a plurality of sections such as short section 4 and 6, and a longer section 8 by transverse scoring. Preferably, the transverse scoring is achieved by the formation of V-shaped notches such as 10 and 12, the notches being opposed in pairs on opposite sides of bar 2. The transverse scoring allows the bar to be broken manually by the application of a bending moment, and the score lines are preferably spaced in the lengthwise direction of the bar by a distance of about one inch so that the bar can be broken to provide a shortened bar having one of a number of predetermined discrete lengths differing in one inch increments. Section 8 is longer, being preferably four inches long. The bar of FIG. 1 is fourteen inches long, there being one four inch section 8 and ten short sections corresponding to sections 4 and 6.

Each of the short sections has a transverse hole, the direction of which is preferably perpendicular to the score lines. Examples of these transverse holes are shown at 14 and 16 in sections 4 and 6 respectively. The holes are preferably through holes extending from one face of the bar to the other. One such hole is provided in the section (not shown) at the extreme right-hand end of the bar, and a similar hole (not shown) is provided at the extreme left-hand end of the bar in section 8. The holes at the opposite ends of the bar are used to mount a pair of articulated joints generally designated 18 and 20. If the bar is shortened by breaking off one or more sections, the hole in the section at the extreme right-hand end of the shortened bar is used to secure articulated joint 20 to the bar. An additional hole 22 is provided in the middle of section 8 for the attachment of a stabilizer rod under certain circumstances as will be described subsequently with reference to FIGS. 13, 14 and 15.

The construction of the lockable articulated joints will be best understood from FIGS. 2 and 3 which illustrate respectively the external and internal details of joint 20.

In a socket member 24, there is formed a concave, substantially spherical surface 26, which acts as a socket for receiving a hollow spherical member 28. Member 28 has a substantially spherical outer surface, the radius of curvature of which approximates the radius of curvature of concave surface 26. While the radii of curvature are approximately equal, they are not necessarily exactly equal. In fact it is advantageous to form the spherical outer surface of member 28 so that its radius of curvature is just slightly larger than the radius of curvature of concave surface 26 in socket member 24. The difference, which may be of the order of a few thousandths of an inch, improves the ability of the joint to be locked securely against articulating movement by the locking means which is about to be described as will be explained more fully with reference to FIG. 16.

Spherical member 28 is also provided with a substantially spherical concave inner surface 30, which is approximately concentric with the outer surface of member 28. Member 28 is provided with an opening 32 which connects its inner and outer surfaces. Opening 32 is preferably circular, and subtends an angle of at least approximately 60° referred to the center of spherical member 28. A locking screw 34 extends through a hole 36 at the end of section 8 of the bar, through a hole 38 in socket member 24, and through hole 32. Locking screw 34 is threaded into a locking member 40, which has a threaded central opening 42 and a convex spherical outer surface 44 adapted to engage inner surface 30 of spherical member 28. The radius of curvature of surface 44 is approximately that of inner surface 30 of spherical member 28. Again, the radius of curvature of surface 44 is made just slightly larger than that of concave surface 30, as will be explained in detail.

The spherical part of locking member 40 is preferably bounded by a circular edge 46, and subtends an angle greater than the angle subtended by hole 32. When the locking screw is loose, locking member 40 allows universal articulation between socket member 24 and spherical member 28, while still preventing separation of the two members. Tightening of screw 34, however, urges the convex outer surface 44 of locking member 40 against inner surface 30 of spherical member 28. The locking member clamps spherical member 28 in socket member 24 so that members 24 and 28 are held tightly in a fixed relationship. Screw 34 preferably has a narrowed portion 50 at the location of holes 32 in order to permit a greater angular movement of spherical member 28.

The bar fits into a slot 52 formed in the underside of socket member 24. The slot is preferably rectangular, having a cross-section substantially conforming to the cross-section of the bar. The conformity of the cross-sections of the slot and the bar prevents socket member 24 from rotating with respect to the bar. By reason of the existence of the slot, it is possible for a single fastener, namely locking screw 34, to be used not only to control locking of the articulating members of the joint, but also to secure the socket member to the bar. Preferably, the vertical dimension of the slot, as viewed in FIG. 3, is made equal to the vertical dimension of the bar so that the bar is flush with the face 54 on the underside of socket member 24. The slot is preferably a blind slot having an end wall at 56. The flush relationship of the bottom of the bar to face 54, and the presence of end wall 56 protect any sharp edges of the bar which might result from breaking at the score lines, from exposure. This prevents the sharp edges at the ends of the bar or at the ends of the part thereof which is used from tearing bed sheets or causing bodily injury. The circular edge of face 54 is preferably rounded as shown in FIGS. 2 and 3 for the same reason.

Formed integrally with hollow spherical member 28 is a clip means 58, which is substantially flat member having bevelled edges for cooperation with a shoe clip 60 (FIGS. 1, 2 and 3). The details of the clip means and shoe clip will be understood from reference to FIGS. 4, 5, 6 and 7, which illustrate the details of a typical shoe clip and its cooperating clip means.

In FIG. 4, there are illustrated in exploded form the elements of articulated joint 20, shown at the right-hand side of FIG. 1. The assembly is fastened to end section 62 of bar 8 by means of a screw 64 which extends upwardly through hole 66 in section 62, through hole 68 in socket member 70, through hole 72 in hollow spherical member 74, and which threads into the bottom of threaded hole 76 in spherical locking member 78.

The clip means 80, which is integral with hollow spherical member 74, is provided with bevelled edges 82 and 84, which interlock with undercut ribs 86 and 88 of shoe clip 90 to provide for the sliding engagement of the clip means 80 with the track formed by ribs 86 and 88 in shoe clip 90. The relationship between the clip means and the shoe clip provides for the engagement of the respective members in a single direction, denoted by the double-ended arrow, substantially parallel to the sole of the shoe to which shoe clip 90 is secured. When the clip means and the shoe clip are engaged, they can only be moved relative to each other in this direction. A latching device is provided to lock the clip means and the shoe clip against any relative movement. The latch means will be best understood from reference to FIGS. 5, 6 and 7.

As shown in FIGS. 5 and 7, clip means 80 is provided with an integral, resilient, flexible arm 92, which extends outwardly from the main body of clip means 80 in a generally parallel relation to edges 82 and 84. Arm 92 is provided with a rectangular projection 94. Because of the resiliency of arm 92, the position of the projection can be changed in the vertical direction as shown in FIG. 7 by manipulation of the end 96 of the arm. The resiliency of the arm urges projection 94 in the upward direction (as viewed in FIG. 7) so that the projection is received in a retaining slot 98 formed in a shoe clip 90.

As shown in FIGS. 6 and 7, shoe clip 90 is attached to the sole 100 of a shoe. The attachement is preferably achieved by the use of a suitable quick-hardening adhesive. This allows the shoe clip to be readily and easily applied to the sole of an ordinary infant's shoe without the use of any tools. Consequently, the shoe clip can be applied easily by the orthopedist himself in his own office immediately prior to the initial adjustment of the lockable articulated joints. Alternatively, the shoe clip can be secured to the sole of the shoe by suitable screws or rivets, countersunk holes being provided in the shoe clip at 102, 104 and 106.

The arm and projection 94 of the clip means are so designed in relation to the shoe clip that projection 94 is urged into retaining slot 98 when the projection and the retaining slot are aligned in registry with each other. At the same time, bevelled edges 82 and 84 of the clip means are held by undercut ribs 86 and 88 of the shoe clip, the resilience of arm 92 urging the bevelled edges 82 and 84 into engagement with the conforming undercut portions or ribs 86 and 88. As a consequence of this relationship, it would normally be necessary to urge the main body of the clip means and its arm in opposite directions in order to establish an initial engagement of the clip means and the shoe clip. The difficulty in engagement of the shoe clip and the clip means is greatly reduced by the provision of an elongated slot 108 arranged to receive projection 94 before the edges 82 and 84 of the clip means are engaged underneath undercut ribs 86 and 88 of the shoe clip. Slot 108 has its long dimension parallel to the direction in which the clip means and shoe clip move relative to each other as they are engaged, and it is relatively deep at end 110 and gradually becomes shallower in the direction toward retaining slot 98. Slot 108 receives projection 94, thereby reducing the flexing of arm 92 as the shoe clip and clip means are initially engaged. As a result, resilient arm 92 can be quite stiff, thus insuring a secure engagement in retaining slot 98, yet the stiffness of the arm poses little difficulty in the engagement of the clip means in the shoe clip. Between slot 108 and retaining slot 98 there is provided a ramp 112 on which projection 98 rides as it approaches the retaining slot. Ramp 112 allows the retaining slot to have a greater depth than it would otherwise have.

The clip means is disengaged from the shoe clip by applying pressure to end 96 of arm 92 to disengage projection 94 from retaining slot 98. When the projection is disengaged from its retaining slot, the clip means and the shoe clip can be disengaged from each other readily by relative movement in the opposite direction from the direction in which they were engaged. The length of the arm is such in relation to the shoe clip that its end overhangs the end of the shoe clip as shown in FIG. 7 so that it can be easily manipulated.

The apparatus which has just been described has a great deal of versatility. Adduction, and abduction are controlled by breaking the bar at a chosen pair of opposed score lines to provide a shortened bar of the desired length. Rotation of the feet is controlled by rotation of hollow spherical member 28 (as viewed in FIG. 2) about the axis of locking screw 34. A visible index means comprising at least one line 114 is provided on the outside of the hollow spherical member. Line 114 corresponds to a line of longitude on the globe. Line 114 is adapted to be viewed in conjunction with index means on socket member 24, comprising a plurality of markings exemplified by markings 116, located around edge 118, which forms the periphery of concave surface 26 (FIG. 3). Marks 116 are preferably evenly spaced as, for example, by ten degrees of angle, and preferably extend vertically on the outside of socket member 24 for good visibility. Desirably, at least some of markings 116 are provided with numerical values, in degrees, as shown in FIG. 2. A zero degree marking is positioned in conjunction with line 114 so that when line 114 is aligned with this zero degree marking, the rotation angle of the foot is zero.

Circular lines 120, corresponding to lines of latitude on the globe extend in parallel around spherical member 28, and are adapted to be brought into tangency with edge 118 by the tilting of member 28 in any direction. Lines 120 are preferably spaced from each other uniformly, as by ten degrees of angle, and are preferably numbered as shown in FIG. 2. Flexion, either plantar or dorsi, and inversion or eversion, or combinations thereof are achieved by tilting spherical member 28 in an appropriate direction and an appropriate extent. The rotation angle, and the flexion and inversion/eversion angle are very accurately reproducible by taking into account the correspondence between line 114 and markings 116, and also by taking into account the relationship between lines 120 and edge 118 of the socket member.

The initial installation of the appliance which has just been described is achieved in the following manner. First, the bar is broken, if necessary, along the desired score line. Desirably, the score lines are numbered, as shown in FIG. 12, the number adjacent a given line indicating the length of the remaining bar, when broken at that particular line. Specifically, the number indicates the distance in inches between the axes of the locking screws, when the articulated joint assemblies are secured in the holes at opposite ends of the shortened bar.

The shoe clips are secured to the soles of the patient's shoes, which may be either a pair of ordinary shoes, or special shoes if desired. Preferably, the shoe clips are attached to the soles of the shoe by means of a fast-hardening adhesive, although screws, rivets or other fastening means may be used alternatively if desired.

The shoes, having the shoe clips attached to them, are then placed on the patient, and the bar and articulated joints are first assembled and then secured to the shoe clips. The articulated joints are adjusted, and then locked by tightening the locking screws. The settings of the articulated joints are then noted by the physician for future reference.

All of the foregoing steps involved in the initial installation can be accomplished by the physician in his own office. This saves the patient a great deal of time, since heretofore it was necessary for the patient to make one or more trips between the physician's office and the orthopedic shoe store where the appliance was obtained and adjusted in accordance with the physician's prescription.

By reason of the fact that the structure includes the slidably engageable clip means and shoe clips as described, and the visible index means shown in FIG. 2, the patient's parent can easily remove and replace the apparatus without disturbing its setting, and can check the setting to be sure it is in accordance with the prescription very easily. In addition, in some instances it may be necessary for the parent to change the setting in accordance with the physician's instructions, and this can be accomplished easily, as the apparatus can be adjusted while it is detached from the patient's shoes. If desired, the apparatus can be taken to the physician's office for adjustment without the need for the patient to be present.

The extension apparatus, shown in FIGS. 8–11, is used in conjunction with the apparatus described above in order to connect one of the lockable articulated joints rigidly to an end of the bar at a fixed perpendicular distance. The purpose of the extension is to provide an increased distance between one of the patient's feet and the corresponding end of the bar so that a downward pressure exerted by the foot through the extension effects pronation of the other foot.

The extension, generally indicated at 122 in FIG. 8, is connected at its lower end to the left-hand end of bar 124. A lockable articulated joint, identical to the one shown in FIG. 2, is secured to the upper end of extension 122.

Extension 122, as shown in detail in FIGS. 9, 10 and 11, comprises a C-shaped member having at its upper end a projection 126 which conforms to the shape of the slot in the bottom of socket member 128 (FIG. 8) of lockable articulated joint 126. Projection 126 fits into the blind slot in socket member 128 in the same way in which bar 124 would fit into the slot if the extension were not used. Projection 126 is provided with a hole 130 through which locking screw 132 extends. The locking screw secures the articulated joint to extension 122, and also locks the relatively movable members of the joint in the desired relationship. Socket member 128 is prevented from rotating with respect to extension 122 by the engagement of projection 126 in the slot of socket member 128.

The lower portion 134 of the extension is provided with a slot 136 which conforms to the cross-section of bar 124, and receives the end of the bar. Lower portion 134 of the extension is secured to the bar by means of a screw 138, which is threaded into threaded hole 140 (FIGS. 9 and 11). Screw 138 locks the extension to the end of the bar, and the relationship of the cross-sections of the bar and slot 136 prevents the extension from rotating with respect to the bar. Consequently, the lockable articulated joint 126 is held securely to the bar by the extension in fixed relationship.

The extension is preferably so designed as to increase the distance between the lockable joint and the bar by about two inches. It should be noted that the design of the extension is such that two or more identical extensions can be nested together to produce increased distances between the lockable joint and the bar.

Figure 15:
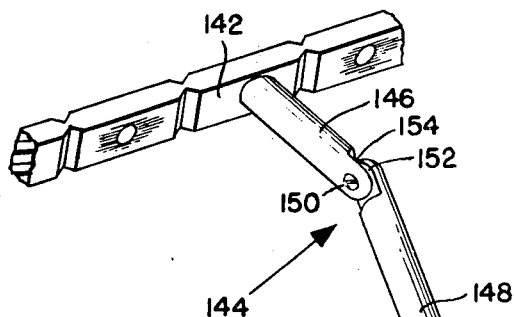
FIG. 15 is an oblique perspective of the stabilizer.

The stabilizer in accordance with the invention is illustrated in FIGS. 13, 14 and 15. FIG. 15 shows a bar 142 with a stabilizer generally indicated at 144 attached to one of the sections of the bar by means of a screw (not shown) which extends through one of the holes in the bar, and which is threaded into a first member 146 of the stabilizer. A second member 148 of the stabilizer is connected to first member 146 in articulating relationship. A locking screw 150 extends through a hole in member 146, and is threaded into a threaded hole in member 148 to lock the two members together in the desired relationship. Members 146 and 148 may be of any desired cross-sectional shape. However, a circular cylindrical shape, as shown, is preferred. Flat surfaces 152 and 154 are formed at the ends of members 146 and 148 which are engaged with each other. These flat surfaces can be roughened or provided with serrations to improve the resistance of the two members against relative movement when they are locked together by tightening screw 150.

FIG. 13 illustrates one possible way in which stabilizer 144 can be used. In this case, the objective is to maintain dorsi flexion in a patient who normally sleeps in a supine position. A stabilizer 156 is secured in perpendicular relationship to an intermediate hole in bar portion 158 in such a way that it extends in a perpendicular direction from the bar in a direction away from the patient. The two articulated members of the stabilizer are locked together in a relationship which produces the desired degree of flexion when end 160 of the stabilizer is in contact with the surface on which the patient is resting, as it normally will be. The articulated joints at the ends of the bar can be adjusted individually in order to produce a different degree of flexion for each of the patient's feet.

In FIG. 14, the objective is to maintain plantar flexion in a patient who tends to sleep in the prone position. A stabilizer 162 is secured to the bar at an intermediate location so that it extends in a direction perpendicular to the bar and away from the patient. The stabilizer is adjusted and locked so that it produces the desired degree of plantar flexion when its end 164 is in contact with the surface on which the patient is resting. In this case, a second stabilizer 166 is desirably used to prevent the patient from defeating the function of stabilizer 162 by bending his knees, as bending of the knees would move stabilizer 162 out of contact with the bed, and allow the patient to move his toes upwardly. Stabilizer 166 is sufficiently long to extend toward the trunk of the patient slightly beyond his knees. As he attempts to bend his knees, stabilizer rod 166 tends to lift the knees off the bed. Consequently, it prevents the patient from bending the knees without exerting considerable effort. Stabilizer rod 166 can be a straight rod, or it can be an articulated stabilizer identical to stabilizer 162.

Still referring to FIG. 14, a single stabilizer can be used alone to maintain dorsi flexion in a patient who tends to sleep in the prone position. Such a stabilizer would extend in the direction of stabilizer 166, and its two members would be locked in a relationship to achieve the desired degree of flexion. No additional stabilizer would be required to prevent the patient from bending his knees in this instance.

Returning to FIG. 13, plantar flexion can be maintained in a patient who sleeps in the supine position by providing an articulated stabilizer which extends from bar 158 toward the trunk of a patient, and the two elements of which are locked together in a relationship such as to produce the desired degree of plantar flexion. The patient in the supine position can defeat the stabilizer by bending his knees, thereby drawing his feet toward his body. Consequently, an additional stabilizer, in the position of stabilizer 156 is used to prevent this. The additional stabilizer is preferably of the articulated type, and is adjusted so that its end is in contact with the surface on which the patient is sleeping.

To summarize the above, with a patient who sleeps in the supine position, dorsi flexion can be achieved by a single articulated stabilizer extending downwardly, and plantar flexion can be achieved by an upwardly extending articulated stabilizer with the aid of a second, downwardly extending stabilizer to prevent the patient from defeating the function of the upwardly extending stabilizer. With a patient who sleeps in the prone position, plantar flexion is maintained by a downwardly extending articulated stabilizer, and an upwardly extending stabilizer is used to prevent the patient from defeating the function of the downwardly extending stabilizer. Dorsi flexion can be maintained in a prone patient by the use of a single upwardly extending articulated stabilizer.

The stabilizers can be secured to any of the intermediate transverse holes in the bar, as shown. Even when the bar is broken at the score line labeled with the numeral "4", as seen in FIG. 12, intermediate hole 22 in section 8 may be used for the attachment of the stabilizer.

The appliance described above is useful in the correction of a wide variety of common lower extremity deformities, including such conditions as internal tibial tortion, external tibial tortion, windswept deformities, metorasis odductus, acetabular dipsplasia, club foot, genu varum (bow legs), as well as various other less common conditions.

The apparatus can be made from various materials. One suitable material is a polymer plastic known as ABS, a synthetic resin from the acrylonitrile-butadiene-styrene family of thermoplastics. ABS has the advantages of a high impact strength and a high strength/weight ratio, can be easily injection molded, and is highly flame retardant. Various other polymer plastics, and even metals, such as aluminum can be used. In all cases, however, the locking screw 34 (FIG. 3) and locking member 40 into which the screw is threaded are preferably metal. Likewise, the various other screws used in the appliance are preferably metal screws.

The appliance described above will normally be supplied in disassembled form as a kit. However, the term "kit" as used herein is intended to include within its scope not only the elements of the apparatus in disassembled form, but the assembled apparatus as well.

FIG. 16 shows, in somewhat exaggerated form, the details of a lockable articulated joint in accordance with the invention. As mentioned previously, this joint is usable in a wide variety of devices other than the foot orthosis appliance described above.

As shown in FIG. 16, the articulated joint comprises a socket member 168, a hollow frusto-spherical member 170, a locking member 172, and a locking screw 174 which extends through a hole 176 in the socket member, a large hole 178 in hollow spherical member 170 and is threaded into a threaded hole 180 in locking fastener 172. A bar 182 is shown, though it is not necessary in devices other than the foot orthosis appliance specifically described above.

The socket member has a concave, substantially frusto-spherical socket 184 having a center of curvature at $C_s$.

Hollow spherical member 170 has a substantially frusto-spherical outer surface 186, and a substantially frusto-spherical inner surface 188. Surfaces 186 and 188 are approximately concentric, having a common center of curvature at $C_h$. Locking member 172 has a substantially frusto-spherical outer surface 90 having a center of curvature at $C_l$.

While the radius of curvature of surface 186 is approximately equal to that of surface 184, the radius of curvature of surface 186 is nevertheless slightly greater than that of surface 184 so that as locking screw 174 is tightened, surfaces 186 and 184 first come into contact with each other along a circular line of contact located at or very near the periphery of the socket surface 184. The difference between the radii of curvature of surfaces 184 and 186 is typically a few thousandths of an inch, for example 0.005 inch. This slight difference in curvature between the two engaging surfaces allows the articulated elements to be locked together in an extremely tight relationship, even though relatively little force is applied to the locking screw.

In a similar manner, the radius of curvature of surface 190 of locking member 172 is slightly greater than that of the inner surface 188 of hollow member 170. Again, the difference is typically only a few thousandths, 0.005 inch. This difference causes the two surfaces 190 and 188 to come into contact with each other, as the locking fastener is tightened, along a circular line of contact located at or near the periphery of locking member 172. This insures an extremely tight locking relationship between locking member 172 and spherical member 186.

Although it is possible for only one pair of the two pairs of engaging surfaces to differ in curvature with a beneficial result, the best results are obtained when the difference in curvature exists in both pairs of engaging surfaces, as illustrated in FIG. 16.

Where two engaging surfaces have different radii of curvature, at least one of the two surfaces should be somewhat resilient at the locations which engage the other of the two surfaces within the range of articulation permitted by hole 178 and locking screw 174.

Figure 17:
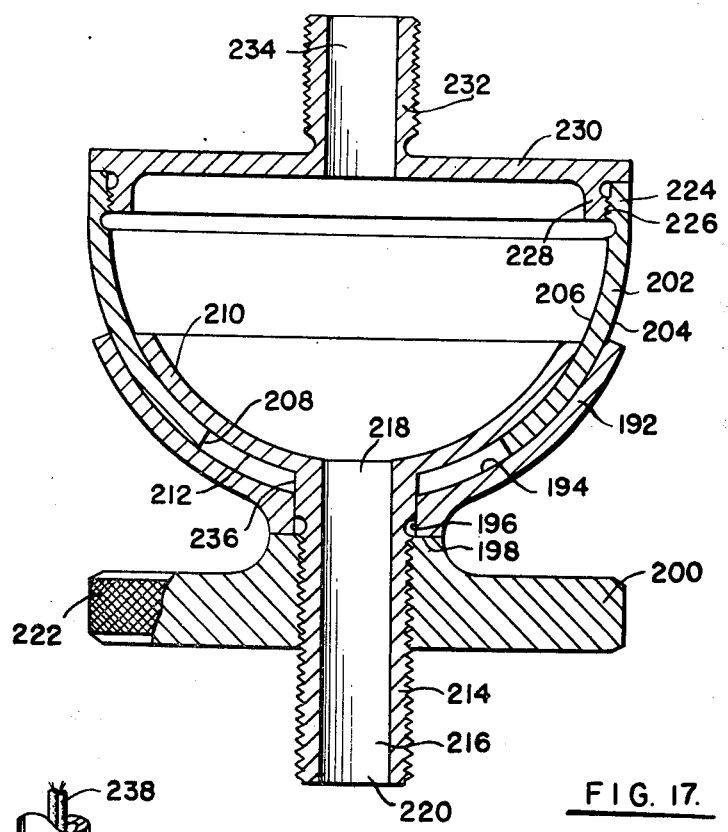

In FIG. 17, a modified version of the lockable articulated joint is shown, this version being particularly adapted for use in supporting various electrical lighting fixtures or other elements requiring electrical power. The articulated joint of FIG. 17 is constructed with a hollow passage in the fastener which allows an electrical power cord to pass through the fastener to the lamp or other electrical fixture which is supported by the lockable joint.

The joint comprises a socket member 192 having a concave, substantially spherical socket 194. A hole 196 extends through the socket member from surface 194 to the opposite side of the socket member, the hole preferably terminating in a flat surface 198 adapted to cooperate with a nut 200 which is used to pull the locking member of the assembly against hollow spherical member 202.

Member 202 has a substantially spherical outer surface 204 having a radius of curvature approximately that of socket surface 194. Member 202 also has a substantially spherical inner surface 206 which is approximately concentric with outer surface 204. A hole 208 extends through member 202 from the inner surface to the outer surface, and is adapted to permit a locking fastener to extend through member 202. Hole 208 is sufficiently large to allow universal articulation between socket member 192 and spherical member 202 through a limited range of movement.

The locking member 210 has a substantially spherical outer surface 212. Surface 212 has a radius of curvature approximating that of surface 206, and is adapted to engage surface 206 for the purpose of clamping the hollow spherical member 202 in fixed relationship with socket member 192.

The locking fastener in this assembly comprises a threaded tubular neck 214 on locking member 210. Neck 214 is externally threaded, and is hollow, having a tubular passage 216 open at end 218 to the interior of the hollow spherical member 202, and open at its other end 220 to the exterior of socket member 192. Nut 200 is threaded onto the external threads of neck 214, and preferably has a knurled periphery 222 so that the assembly can be readily locked in the desired position and released for adjustment to a new position.

Hollow spherical member 202 preferably has a short, substantially cylindrical portion 224 having internal threads 226 adapted to receive a threaded cylindrical projection 228 on plate 230. Plate 230 has a hollow, externally threaded neck 232, having an internal passage 234 providing communication between the interior of member 202 and the exterior thereof.

It will be observed that the threads on neck 232 can be used to secure hollow spherical member 202 to a support, and the threads on neck 214 which extend beyond nut 200 can be used to secure the locking member (and thereby the socket) to a fixture. Desirably, portion 236 of neck 214, near locking member 210, is an unthreaded cylinder having a diameter such that it closely fits hole 196 in socket member 192. This maintains the relationship between the socket and locking member 210.

Figure 18:
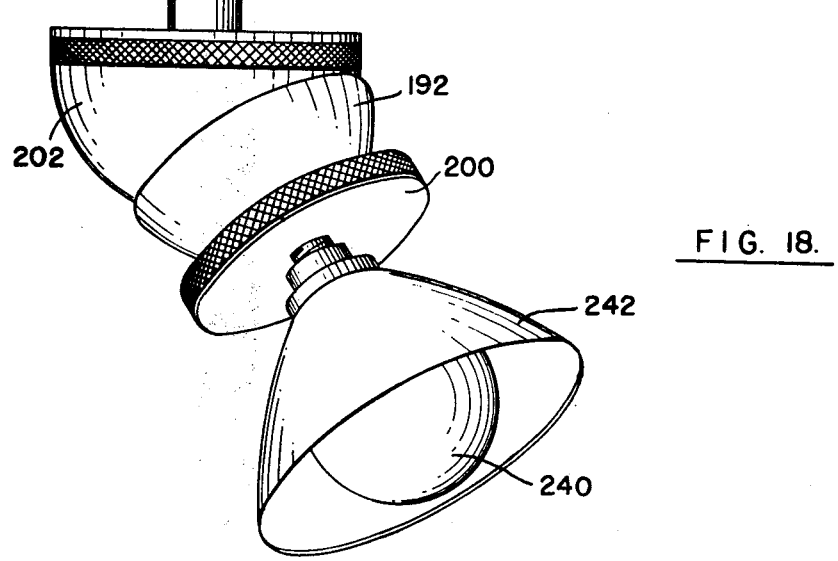
FIG. 18 is an oblique perspective view of a lighting fixture supported by the joint of FIG. 17.

Hollow passages 234 and 220 permit an electrical power cord to pass through the articulated joint assembly in a completely hidden manner. Thus, as shown in FIG. 18, an electrical power cord 238 is used to power bulb 240 in fixture 242. Power cord 238 extends downwardly through conduit 244, which is threaded onto neck 232 (FIG. 17) to support hollow spherical member 202, which in this case is the fixed portion of the assembly. Fixture 242 is threaded onto the external threads of neck 214. Repositioning of fixture 242 is accomplished simply by turning nut 200 in the counterclockwise direction, repositioning the movable part of the assembly, and retightening nut 200.

The dimensional relationships between the socket, the inner and outer spherical surfaces of the hollow member, and the operative spherical surface of the locking member are preferably related to each other in the same manner as are the corresponding parts of the lockable joint in FIG. 16. The joint of FIG. 17, may, of course, be used for numerous purposes other than the one specifically illustrated in FIG. 18.

I claim:

1. A lockable articulated joint comprising:
   a socket member having a concave, substantially frusto-spherical socket surface, and a hole extending from the concave socket surface to the opposite side of said socket member;
   a hollow member having a substantially frusto-spherical outer surface with a radius of curvature approximating that of said socket surface, a substantially frusto-spherical inner surface approximately concentric with said outer surface, and means providing a hole extending from said inner surface to said outer surface to permit a locking fastener to extend through the hollow spherical member while allowing universal articulation between said socket and said frusto-spherical member through a limited range, said hollow member extending into and engaging said socket member;
   a locking member having a substantially frusto-sperhical outer surface engaging the inner surface of said hollow member and having a radius of curvature approximating that of the inner surface of said hollow member; and
   a locking fastener extending through the hole in said socket member and the hole in said hollow member, and comprising means for releasably forcing said locking member toward said socket member to clamp said hollow member therebetween in a fixed relationship to said socket member;
   the radius of curvature of the outer surface of said locking member being slightly greater than that of the inner surface of said hollow member, and at least one member of said locking member and said hollow member being resilient at the locations on its surface which engage the other of said locking and hollow members within said limited range of articulation.

2. A lockable articulated joint according to claim 1 wherein the radius of curvature of the outer surface of said hollow member is slightly greater than that of the socket surface, and at least one member of said hollow member and said socket member being resilient at the locations on its surface which engage the other of said hollow and socket members within said limited range of articulation.

3. A lockable articulated joint comprising:
   a socket member having a concave, substantially frusto-spherical socket surface, and a hole extending from the concave socket surface to the opposite side of said socket member;
   a hollow member having a substantially frusto-spherical outer surface with a radius of curvature approximating that of said socket surface, a substantially frusto-spherical inner surface approximately concentric with said outer surface, and means providing a hole extending from said inner surface to said outer surface to permit a locking fastener to extend through the hollow spherical member while allowing universal articulation between said socket and said frusto-spherical member through a limited range, said hollow member extending into and engaging said socket member;
   a locking member having a substantially frusto-spherical outer surface engaging the inner surface of said hollow member and having a radius of curvature approximating that of the inner surface of said hollow member; and
   a locking fastener extending through the hole in said socket member and the hole in said hollow member, and comprising means for releasably forcing said locking member toward said socket member to clamp said hollow member therebetween in a fixed relationship to said socket member;
   the radius of curvature of the outer surface of said hollow member being slightly greater than that of the socket surface, and at least one member of said hollow member and said socket member being resilient at the locations on its surface which engage the other of said hollow and socket members within said limited range of articulation.

* * * * *